US008466327B2

(12) United States Patent
Arthur

(10) Patent No.: US 8,466,327 B2
(45) Date of Patent: Jun. 18, 2013

(54) ALDEHYDE-FUNCTIONALIZED POLYETHERS AND METHOD OF MAKING SAME

(75) Inventor: Samuel David Arthur, Wilmington, DE (US)

(73) Assignee: Actamax Surgical Materials, LLC, Berkeley, CA (US)

( * ) Notice: Subject to any disclaimer, the term of this patent is extended or adjusted under 35 U.S.C. 154(b) by 827 days.

(21) Appl. No.: 12/550,456

(22) Filed: Aug. 31, 2009

(65) Prior Publication Data

US 2010/0125155 A1 May 20, 2010

Related U.S. Application Data

(60) Provisional application No. 61/115,980, filed on Nov. 19, 2008.

(51) Int. Cl.
C07C 41/00 (2006.01)
C07C 47/00 (2006.01)
C07C 315/00 (2006.01)

(52) U.S. Cl.
USPC .............................. 568/579; 568/420; 568/18

(58) Field of Classification Search
USPC ........................................ 568/579, 420, 18
See application file for complete search history.

(56) References Cited

U.S. PATENT DOCUMENTS

| | | |
|---|---|---|
| 4,584,188 A | 4/1986 | Graham |
| 4,703,116 A | 10/1987 | Solarek et al. |
| 4,731,162 A | 3/1988 | Solarek et al. |
| 4,741,804 A | 5/1988 | Solarek et al. |
| 4,749,800 A | 6/1988 | Jobe et al. |
| 4,766,245 A | 8/1988 | Larkin et al. |
| 5,092,883 A | 3/1992 | Eppley et al. |
| 5,116,824 A | 5/1992 | Miyata et al. |
| 5,162,430 A | 11/1992 | Rhee et al. |
| 5,196,441 A | 3/1993 | Kunisch et al. |
| 5,275,838 A | 1/1994 | Merrill |
| 5,292,802 A | 3/1994 | Rhee et al. |
| 5,308,889 A | 5/1994 | Rhee et al. |
| 5,324,775 A | 6/1994 | Rhee et al. |
| 5,328,955 A | 7/1994 | Schaulin et al. |
| 5,451,398 A | 9/1995 | Vigh |
| 5,502,042 A | 3/1996 | Gruskin et al. |
| 5,505,952 A | 4/1996 | Jiang et al. |
| 5,514,379 A | 5/1996 | Weissleder et al. |
| 5,567,685 A | 10/1996 | Linden et al. |
| 5,643,575 A | 7/1997 | Martinez et al. |
| 5,733,563 A | 3/1998 | Fortier |
| 5,830,986 A | 11/1998 | Merrill et al. |
| 5,840,698 A | 11/1998 | Campbell et al. |
| 5,843,865 A | 12/1998 | Del Corral et al. |
| 5,874,500 A | 2/1999 | Rhee et al. |
| 6,051,648 A | 4/2000 | Rhee et al. |
| 6,121,375 A | 9/2000 | Eknoian |
| 6,150,472 A | 11/2000 | Engbers |
| 6,165,488 A | 12/2000 | Tardy et al. |
| 6,166,130 A | 12/2000 | Rhee et al. |
| 6,323,278 B2 | 11/2001 | Rhee et al. |
| 6,391,939 B2 | 5/2002 | Tayot et al. |
| 6,410,519 B1 | 6/2002 | Gruskin et al. |
| 6,458,147 B1 | 10/2002 | Cruise et al. |
| 6,458,889 B1 | 10/2002 | Trollsas et al. |
| 6,465,694 B1 | 10/2002 | Baudys et al. |
| 6,514,534 B1 | 2/2003 | Sawhney |
| 6,534,591 B2 | 3/2003 | Rhee et al. |
| 6,602,952 B1 | 8/2003 | Bentley et al. |
| 6,620,125 B1 | 9/2003 | Redl |
| 6,696,089 B2 | 2/2004 | Kabanov et al. |
| 6,703,047 B2 | 3/2004 | Sawhney et al. |
| 6,756,518 B2 | 6/2004 | Gruskin et al. |
| 6,800,278 B1 | 10/2004 | Perrault et al. |
| 6,833,408 B2 | 12/2004 | Sehl et al. |
| 6,858,736 B2 | 2/2005 | Ngo et al. |
| 7,217,845 B2 | 5/2007 | Rosen et al. |
| 7,834,065 B2 | 11/2010 | Nakajima et al. |
| 7,960,498 B2 | 6/2011 | Chenault et al. |
| 2002/0151520 A1 | 10/2002 | Gruskin |
| 2003/0022216 A1 | 1/2003 | Mao et al. |
| 2003/0027788 A1 | 2/2003 | Singh et al. |
| 2003/0064502 A1 | 4/2003 | Illman et al. |
| 2003/0087111 A1 | 5/2003 | Hubbell et al. |
| 2003/0108511 A1 | 6/2003 | Sawhney |
| 2003/0119985 A1 | 6/2003 | Sehl et al. |
| 2004/0086479 A1 | 5/2004 | Grinstaff et al. |
| 2004/0096507 A1 | 5/2004 | Kwant et al. |
| 2004/0225097 A1 | 11/2004 | Nho et al. |

(Continued)

FOREIGN PATENT DOCUMENTS

| | | |
|---|---|---|
| EP | 0961783 | 1/2007 |
| JP | 1982-102932 | 6/1982 |

(Continued)

OTHER PUBLICATIONS

J. Milton Harris, Laboratory Synthesis of Polyethylene Glycol Derivatives, J. Macromol Sci.—Rev. Macromol. Chem Phys. C25(3), 325, 342-345, 366, 367, 370 and 371 (1985).

J. Milton Harris et al., Synthesis and Characterization of Poly(Ethylene Glycol) Derivatives, J. Polymer Sci. Polymer Chem. Ed. 22, 341 and 347 (1984).

J. Milton Harris et al., Synthesis of New Poly(Ethylene Glycol) Derivatives, Poly(Ethylene Glycol) Chemistry: Biotechnical and Biomedical Applications, J. Milton Harris, Ed.; Plenum Press, New York, 1992, Chapter 22, p. 371, 376 and 377.

Thome, J., et al., "Ultrathin Antibacterial Polyammonium Coatings on Polymer Surfaces"; Surface and Coatings Technology, 174-175, 2003, pp. 584-587.

(Continued)

Primary Examiner — Johann R Richter
Assistant Examiner — Kofi Adzamli
(74) Attorney, Agent, or Firm — McCarter and English

(57) ABSTRACT

Aldehyde-functionalized polyethers containing thiomethylaldehyde groups are described. Also described is a method of preparing the aldehyde-functionalized polyethers. These functionalized polyethers may be useful for protein conjugation, surface modification, and for the formation of hydrogel adhesives and sealants which are useful for medical applications.

15 Claims, No Drawings

U.S. PATENT DOCUMENTS

| | | | |
|---|---|---|---|
| 2004/0235708 | A1 | 11/2004 | Rhee et al. |
| 2005/0002893 | A1 | 1/2005 | Goldmann |
| 2005/0020805 | A1 | 1/2005 | Sunkara et al. |
| 2005/0288684 | A1 | 12/2005 | Aronson et al. |
| 2006/0078536 | A1 | 4/2006 | Kodokian et al. |
| 2006/0115531 | A1 | 6/2006 | Chenault |
| 2006/0292030 | A1 | 12/2006 | Odermatt et al. |
| 2007/0031467 | A1 | 2/2007 | Abrahams et al. |
| 2007/0048251 | A1 | 3/2007 | Arthur |
| 2007/0249870 | A1 | 10/2007 | Chenault |
| 2008/0220047 | A1 | 9/2008 | Sawhney et al. |
| 2008/0319101 | A1 | 12/2008 | Nakajima et al. |
| 2009/0035249 | A1 | 2/2009 | Bhatia et al. |
| 2009/0054535 | A1 | 2/2009 | Figuly et al. |
| 2010/0086678 | A1 | 4/2010 | Arthur et al. |
| 2010/0112063 | A1 | 5/2010 | Figuly et al. |
| 2010/0272804 | A1 | 10/2010 | Lu |
| 2011/0269916 | A1 | 11/2011 | Chenault et al. |

FOREIGN PATENT DOCUMENTS

| | | | |
|---|---|---|---|
| JP | 1988-11167 | | 1/1988 |
| WO | WO 87/00836 | | 2/1987 |
| WO | W087/00836 | A1 | 12/1987 |
| WO | WO 90/10441 | | 9/1990 |
| WO | WO 91/15368 | | 10/1991 |
| WO | WO 97/30103 | | 8/1997 |
| WO | WO 99/01143 | | 1/1999 |
| WO | WO 00/69925 | | 11/2000 |
| WO | WO 01/49268 | | 7/2001 |
| WO | WO 01/72280 | | 10/2001 |
| WO | WO 01/87986 | | 11/2001 |
| WO | WO 02/102864 | | 12/2002 |
| WO | WO 03/020818 | | 3/2003 |
| WO | WO 03/097759 | | 11/2003 |
| WO | WO 2006/031358 | | 3/2006 |
| WO | WO 2006/042161 | | 4/2006 |
| WO | WO 2006/080523 | | 8/2006 |
| WO | WO 2006/086510 | | 8/2006 |
| WO | WO 2008/005207 | | 1/2008 |
| WO | WO 2008/066787 | | 6/2008 |
| WO | WO 2009/064977 | | 5/2009 |
| WO | PCT/US09/55485 | | 8/2009 |
| WO | PCT/US09/55487 | | 8/2009 |
| WO | WO 2010/059279 | | 5/2010 |
| WO | WO 2010/059280 | | 5/2010 |
| WO | WO 2010/111570 | | 9/2010 |
| WO | WO 2010/118284 | | 10/2010 |

OTHER PUBLICATIONS

Harris, J. Milton, "Laboratory Synthesis of Polyethylene Glycol Derivatives", JMS—Rev., Macromol. Chem. Phys., C25 (3), 1985, pp. 325-373.

Harris, J. Milton, et al., "Synthesis of New Poly(Ethylene Glycol) Derivatives", PolyEthylene Glycol Chemistry: Biotechnical and Biomedical Applications, edited by Milton J. Harris, Plenum Press: New York, 1992, pp. 371-381.

Chen, Nicole, et al., "Mechanisms of Aldehyde-Containing Paper Wet-Strength Resins", Industrial & Engineering Chemistry Research, vol. 41, No. 22, 2002, pp. 5366-5371.

Callant, Dominique, et al., "A New Approach to Dextran Derivatives with Pendent Aldehyde Groups", Reactive Polymers, vol. 8 , 1988, pp. 129-136.

Hollander, Andreas, et al., "Polymer Surface Chemistry for Biologically Active Materials", Applied Surface Science, vol. 235, 2004, pp. 145-150.

Stone, H. Harlan, et al., "Antibiotic Prophylaxis in Gastric, Biliary and Colonic Surgery", Ann. Surg; Oct. 1976, pp. 443-450.

Fishman, Alexander, et al., "Synthesis and Investigation of Novel Branched PEG-Based Soluble Polymer Supports", The Journal of Organic Chemistry, vol. 68, 2003, pp. 9843-9846.

Newkome, George R., "Improved Synthesis of an Ethereal Tetraamine Core for Dendrimer Construction", The Journal of Organic Chemistry, vol. 67, 2002, pp. 3957-3960.

Halabi, A., et al., "Synthesis and Characterization of a Novel Dendritic Acrylic Monomer", The Journal of Organic Chemistry, vol. 65, 2000, pp. 9210-9213.

Harris, J. Milton, et al., "Synthesis and Characterization of Poly(ethylene Glycol) Derivatives", Journal of Polymer Science: Polymer Chemistry Edition, vol. 22, 1984, pp. 341-352.

Merrill, Edward W., "Poly(ethylene oxide) Star Molecules: Synthesis, Characterization, and Applications in Medicine and Biology", Journal of Biomaterials Science Polymer Edition, vol. 5, No. 1/2, 1993, pp. 1-11.

Zhao, Xuan, et al., "Novel Degradable Poly(ethylene glycol) Esters for Drug Delivery", Poly(ethylene glycol) Chemistry and Biological Applications, Oxford University Press, 1998, Chapter 28, pp. 458-472.

Azzam, Tony, et al., "Cationic Polysaccharides for Gene Delivery", Macromolecules, vol. 35, No. 27, 2002, pp. 9947-9953.

Nagasaki, Yukio, et al., "Formyl-Ended Heterobifunctional Poly(ethylene oxide): Synthesis of Poly(ethylene oxide) with a Formyl Group at One End and a Hydroxyl Group at the Other End", Bioconjugate Chemistry, vol. 6, No. 2, 1995, pp. 231-233.

Greenwald, Richard B., et al., "Drug Delivery Systems Employing 1,4- or 1,6-Elimination: Poly(ethylene glycol) Prodrugs of Amine-Containing Compounds", Journal of Medicinal Chemistry, vol. 42, No. 18, 1999, pp. 3657-3667.

Zalipsky, Samuel, et al., "Preparation and Applications of Polyethylene Glycol-Polystyrene Graft Resin Supports for Solid-Phase Peptide Synthesis", Reactive Polymers, vol. 22, 1994, pp. 243-258.

Lara, V.S., et al., "Dentin-Induced In Vivo Inflammatory Response and In Vitro Activation of Murine Macrophages", Journal of Dental Research, vol. 82, No. 6, 2003, pp. 460-465.

Atassi, M.Z., "Immunochemistry of Proteins", vol. 1, Plenum Press, New York, 1977, pp. 59-60.

Sweeney, Thomas, et al., "Intestinal Anastomoses Detected with a Photopolymerized Hydrogel", Surgery, vol. 131, No. 2, Feb. 2002, pp. 185-189.

Kim, Jae Chan, et al., "Evaluation of Tissue Adhesives in Closure of Scleral Tunnel Incisions", Journal of Cataract & Refractive Surgery, vol. 21, May 1995, pp. 320-325.

Sarayba, Melvin A., et al., "Inflow of Ocular Surface Fluid Through Clear Corneal Cataract Incisions: A Laboratory Model", American Journal of Ophthalmology, vol. 138, No. 2, Aug. 2004, pp. 206-210.

Buckmann, Andreas F., et al., "Functionalization of Poly(ethylene glycol) and Monomethoxy-Poly(ethylene glycol)", Makromolecular Chemistry, vol. 182, 1981, pp. 1379-1384.

Bruce, J., et al., "Systematic Review of the Definition and Measurement of Anastomotic Leak after Gastrointestinal Surgery", British Journal of Surgery, vol. 88, 2001, pp. 1157-1168.

Mo, Xiumei, et al., "Soft Tissue Adhesive Composed of Modified Gelatin and Polysaccharides", Journal of Biomaterials Science Polymer Edition, vol. 11, No. 4, 2000, pp. 341-351.

Hofreiter, B.T., et al., "Rapid Estimation of Dialdehyde Content of Periodate Oxystarch through Quantitative Alkali Consumption", Analytical Chemistry, vol. 27, No. 12, Dec. 1955, pp. 1930-1931.

Zhao, Huiru, et al., "Determination of Degree of Substitution of Formyl Groups in Polyaldehyde Dextran by the Hydroxylamine Hydrochloride Method", Pharmaceutical Research, vol. 8, No. 3, 1991, pp. 400-402.

Kurisawa, Motoichi, et al., "Double-Stimuli-Responsive Degradation of Hydrogels Consisting of Oligopeptide-Terminated Poly(ethylene glycol) and Dextran with an Interpenetrating Polymer Network", Journal of Biomaterials Science Polymer Edition, vol. 8, No. 9, 1997, pp. 691-708.

Pfannemuller, B., et al., "Chemical Modification of the Surface of the Starch Granules", Starch/Starke, vol. 95, No. 9, 1983, pp. 298-303.

ALDEHYDE-FUNCTIONALIZED POLYETHERS AND METHOD OF MAKING SAME

CROSS-REFERENCE TO RELATED APPLICATION

This application claims priority under 35 U.S.C. §119 from U.S. Provisional Application Ser. No. 61/115,980, filed Nov. 19, 2008.

FIELD

Disclosed herein are aldehyde-functionalized polyethers containing at least one thiomethylaldehyde group and a method of making the aldehyde-functionalized polyethers.

BACKGROUND

Aldehyde-functionalized polyethers are generally stable in aqueous solution and are very reactive electrophiles which form reversible bonds to amine-functionalized reactants. These two properties are highly desirable for many applications. For example, aldehyde-functionalized polyethers, and in particular, aldehyde-functionalized polyethylene glycols are useful for protein conjugation, surface modification, and for the formation of hydrogel adhesives and sealants which are useful for medical applications. For the formation of hydrogel adhesives and sealants, an aldehyde-functionalized polyether is reacted with an amine-containing component to form a crosslinked polymeric matrix which acts a sealant.

Various methods are known in the art for the preparation of aldehyde-functionalized polyethers. For example, various oxidative reactions utilizing oxidizing agents such as manganese oxide, pyridinium chlorochromate, or dimethyl sulfoxide-acetic anhydride have been used to convert the terminal hydroxyl groups of polyethylene glycol to aldehyde groups. However, these oxidative reactions are not quantitative and may be accompanied by unwanted side reactions. Additionally, product purification is difficult. Aldehyde-functionalized polyethylene glycols have also been prepared from the diethyl acetal of α-bromoacetaldehyde and by reaction of the polyethylene glycol chloride derivative with the phenoxide of 4-hydroxy-benzaldehyde. Rosen et al. (U.S. Pat. No. 7,217,845) describe aldehyde-functionalized polyethylene glycols that are prepared by functionalizing polyethylene glycol ends with X—$(CH_2)_n$—CHO, where X is O or N and n is from 2 to 8. However, these methods typically result in low yields, require multiple steps, and/or yield a product that is difficult to purify.

Therefore, the need exists for aldehyde-functionalized polyethers that are easy to prepare, can be prepared with readily available reactants, and can be produced in high yield and in pure form.

SUMMARY

The present invention addresses the above need by providing aldehyde-functionalized polyethers containing at least one thiomethylaldehyde group and a method of making the aldehyde-functionalized polyethers.

Accordingly, in one embodiment the invention provides a composition of matter comprising at least one compound of the formula:

OHC—$CH_2$—S—(P)—S—$CH_2$CHO; or    a)

Q[(PA)-S—$CH_2$CHO]$_m$    b)

wherein:
(i) P is a linear polymeric segment terminating with a methylene group at both ends of said segment, wherein said segment is derived from a polymer selected from the group consisting of: polyethylene oxide, poly(trimethyleneoxide), poly(tetramethyleneoxide), block or random copolymers of polyethylene oxide and polypropylene oxide, and triblock copolymers of polyethylene oxide and polypropylene oxide;
(ii) Q is a core molecule consisting of a polyol containing at least a number m of OH groups and with the hydrogen removed from at least m of said OH groups;
(iii) PA is a linear polymeric arm terminating with a methylene group at both ends of said arm, wherein said arm is derived from a polymer selected from polyethylene oxide, poly(trimethyleneoxide), poly(tetramethyleneoxide), block or random copolymers of polyethylene oxide and polypropylene oxide, and triblock copolymers of polyethylene oxide and polypropylene oxide;
(iv) S is a sulfur atom; and
(v) m=2 to 16.

In another embodiment, the invention provides a method for making a composition comprising at least one aldehyde-functionalized polyether comprising the steps of:
a) reacting at a temperature of about 50° C. to about 100° C. in the presence of a base and an optional solvent, 1-thioglycerol and at least one polyether having one or more leaving groups capable of being displaced by the 1-thioglycerol, to form a thiomethylethylene glycol-functionalized polyether having at least one glycol group;
b) separating the thiomethylethylene glycol-functionalized polyether from the optional solvent and unreacted 1-thioglycerol;
c) oxidizing the thiomethylethylene glycol-functionalized polyether separated in step (b) with about one equivalent of an oxidizing agent per glycol group, said oxidizing agent being capable of converting said glycol group to an aldehyde group, at a temperature of about 0° C. to about 50° C. in an aqueous solution to form the aldehyde-functionalized polyether; and
d) recovering said aldehyde-functionalized polyether.

DETAILED DESCRIPTION

As used above and throughout the description of the invention, the following terms, unless otherwise indicated, shall be defined as follows:

The term "aldehyde-functionalized polyether" refers to a polyether that has been chemically modified to contain at least one aldehyde functional group. The aldehyde-functionalized polyethers disclosed herein contain at least one thiomethylaldehyde group.

The term "thiomethylaldehyde" refers to the —$SCH_2CHO$ group, where the open valence of the sulfur is bonded to a carbon atom at the end of a polyether chain.

The term "crosslink" refers to a bond or chain of atoms attached between and linking two different polymer chains.

The term "polyether" refers to a polymer having the repeat unit [—O—R]—, wherein R is a hydrocarbylene group having 2 to 5 carbon atoms. The polyether may also be a random or block copolymer comprising different repeat units which contain different R groups.

The term "hydrocarbylene group" refers to a divalent group formed by removing two hydrogen atoms, one from each of two different carbon atoms, from a hydrocarbon.

The term "branched polyether" refers to a polyether having one or more branch points ("arms"), including star, dendritic, comb, and hyperbranched polyethers.

The term "dendritic polyether" refers to a highly branched polyether having a tree-like structure.

The term "comb polyether" refers to a polyether having a main chain with multiple trifunctional branch points from each of which a linear arm emanates.

The term "star polyether" refers to polyether having a central branch point, which may be a single atom or a chemical group, from which linear arms emanate.

The term "hyperbranched polyether" refers to a highly branched polyether having fewer branches and less regular branching than a dendritic polyether.

The term "% by weight", also referred to herein as "wt %" refers to the weight percent relative to the total weight of the solution or dispersion, unless otherwise specified.

The term "hydrogel" refers to a water-swellable polymeric matrix, consisting of a three-dimensional network of macromolecules held together by covalent or non-covalent crosslinks, that can absorb a substantial amount of water to form an elastic gel.

The term "PEG" as used herein, refers to polyethylene glycol.

The term "EW" as used herein refers to equivalent weight, which is equal to the molecular mass of a compound divided by the number of functional groups to which the equivalent weight pertains.

The term "medical application" refers to medical applications as related to humans and animals.

The meaning of abbreviations used is as follows: "min" means minute(s), "h" means hour(s), "sec" means second(s), "d" means day(s), "mL" means milliliter(s), "L" means liter(s), "μL" means microliter(s), "cm" means centimeter(s), "mm" means millimeter(s), "μm" means micrometer(s), "mol" means mole(s), "mmol" means millimole(s), "g" means gram(s), "mg" means milligram(s), "wt %" means percent by weight, "mol %" means mole percent, "Vol" means volume, "v/v" means volume per volume, "Da" means Daltons, "kDa" means kiloDaltons, the designation "10K" means that a polymer molecule possesses a number-average molecular weight of 10 kiloDaltons, "M" means molarity, "MWCO" means molecular weight cut-off, "kPa" means kilopascals, "$^{1}$H NMR" means proton nuclear magnetic resonance spectroscopy, "ppm" means parts per million, "$M_w$" means weight-average molecular weight, "$M_n$" means number-average molecular weight, "PBS" means phosphate-buffered saline.

Disclosed herein are aldehyde-functionalized polyethers containing at least one thiomethylaldehyde group. The method to prepare the aldehyde-functionalized polyethers is simple, uses readily available reactants, and produces the aldehyde-functionalized polyethers in high yield and in pure form. These aldehyde-functionalized polyethers may be useful for a variety of applications, including protein conjugation, surface modification, and for the formation of hydrogel adhesives and sealants which are useful for medical applications. To form the hydrogel adhesive or sealant, the aldehyde-functionalized polyether is combined with a second component that contains nucleophilic groups that are capable of reacting with the aldehyde groups of the functionalized polyether to form a crosslinked hydrogel. The hydrogels formed using the aldehyde-functionalized polyethers disclosed herein may be useful as an adhesive for medical and veterinary applications including, but not limited to, wound closure, supplementing or replacing sutures or staples in internal surgical procedures such as intestinal anastomosis and vascular anastomosis, tissue repair, ophthalmic procedures, and as a plug to seal a fistula or the punctum. Additionally, the hydrogels may have utility in drug delivery, and in anti-adhesive applications.

Aldehyde-Functionalized Polyethers

The aldehyde-functionalized polyethers disclosed herein can be linear or branched polymers. In one embodiment, the aldehyde-functionalized polyethers are linear polymers having the general formula:

$$\text{OHC—CH}_2\text{—S—(P)—S—CH}_2\text{CHO} \quad (1)$$

In the formula, "P" is a linear polymeric segment terminating with a methylene group at both ends of said segment, wherein said segment is derived from a polymer selected from polyethylene oxide, poly(trimethyleneoxide), poly(tetramethyleneoxide), block or random copolymers of polyethylene oxide and polypropylene oxide, and triblock copolymers of polyethylene oxide and polypropylene oxide. As used herein "derived from a polymer" when referring to a polymeric segment, means that the polymeric segment has the structure of the polymer without the polymer's terminal end groups (e.g., hydroxyl groups), and therefore both ends of the polymeric segment are terminated with a methylene group. In one embodiment, P is derived from polyethylene oxide. In some embodiments, P has a number-average molecular weight of about 200 to about 20,000 Daltons. In other embodiments, P has a number-average molecular weight of about 1,000 to about 100,000 Daltons. In other embodiments, P has a number-average molecular weight of greater than 100,000 Daltons. "S" represents a sulfur atom.

In one embodiment, the aldehyde-functionalized polyether is a linear polyethylene glycol bis(thiomethylaldehyde) having a number-average molecular weight of about 600 Daltons, as described in Example 2 herein.

In another embodiment, the aldehyde-functionalized polyethers are branched polymers having the general formula:

$$\text{Q[(PA)-S—CH}_2\text{CHO]}_m \quad (2)$$

In the formula, Q is a core molecule consisting of a polyol containing at least a number "m" of OH groups and with the hydrogens removed from at least "m" of the OH groups, where "m" is defined below. Suitable polyols include, but are not limited to, glycerol, pentaerythritol, dipentaerythritol, inositol, sorbitol, and polyglycerols, such as hexaglycerol or tetraglycerol. "S" represents a sulfur atom, and "PA" is a linear polymeric arm terminating with a methylene group at both ends of said arm, wherein said arm is derived from a polymer selected from polyethylene oxide, poly(trimethyleneoxide), poly(tetramethyleneoxide), block or random copolymers of polyethylene oxide and polypropylene oxide, and triblock copolymers of polyethylene oxide and polypropylene oxide. In one embodiment, PA is derived from polyethylene oxide. In some embodiments, PA has a number-average molecular weight of about 100 to about 10,000 Daltons. In other embodiments, PA has a number-average molecular weight of about 1,000 to about 100,000 Daltons. The number of arms "m" is from 2 to 16.

In one embodiment, the aldehyde-functionalized polyether is a four-arm polyethylene glycol tetra(thiomethylaldehyde) having a number-average molecular weight of about 2,000 Daltons, as described in Example 1 herein.

Method of Preparing Aldehyde-Functionalized Polyethers

The starting materials used to prepare the linear, aldehyde functionalized polyethers disclosed herein may be linear polymers such as polyethylene oxide, poly(trimethyleneoxide), block or random copolymers of polyethylene oxide and polypropylene oxide or triblock copolymers of polyethylene oxide and polypropylene oxide, having terminal hydroxyl groups. These compounds are available from commercial sources such as Sigma-Aldrich (St. Louis, Mo.), SunBio Inc. (Anyang City, S. Korea), and NOF Corp. (Tokyo, Japan). It should be recognized that these polymers are generally a heterogeneous mixture having a distribution of different molecular weights, and are characterized by an average molecular weight, for example, the weight-average molecular weight ($M_w$), or the number-average molecular weight ($M_n$), as is known in the art. Consequently, the linear, aldehyde-functionalized polyethers derived from these polymers are compositions comprising a heterogeneous mixture having a distribution of different molecular weights.

The starting materials used to prepare the branched, aldehyde-functionalized polyethers may be multi-arm polyether polyols including, but not limited to, comb and star polyether polyols. It should be recognized that the multi-arm polyether polyols are generally a somewhat heterogeneous mixture having a distribution of arm lengths and in some cases, a distribution of species with different numbers of arms. When a polyether polyol has a distribution of species having different numbers of arms, it can be referred to based on the average number of arms in the distribution. For example, an 8-arm star PEG polyol comprises a mixture of multi-arm star PEG polyols, some having less than and some having more than 8 arms; however, the multi-arm star PEG polyols in the mixture have an average of 8 arms. Consequently, the branched, aldehyde-functionalized polyethers derived from these polymers are compositions comprising a heterogeneous mixture. Therefore, the terms "8-arm", "6-arm", "4-arm" and "3-arm" as used herein to refer to multi-arm polyethers and derivatives thereof, should be construed as referring to a heterogeneous mixture having a distribution of arm lengths and in some cases, a distribution of species with different numbers of arms, in which case the number of arms recited refers to the average number of arms in the mixture.

Multi-arm polyether polyols are available commercially from companies such as Nektar Transforming Therapeutics (Huntsville, Ala.), SunBio Corp. (Anyang City, S. Korea), and NOF Corp. (Tokyo, Japan). Alternatively, multi-arm polyether polyols may be synthesized using methods known in the art (see for example, Merrill et. al., U.S. Pat. No. 5,830,986; Hamann et al., EP 540823; and Nho et al., U.S. Patent Application Publication No. 2004/096507). Typically, multi-arm polyether polyols are made by condensing ethylene oxide, propylene oxide or mixtures thereof with a polyol core, such as glycerol, pentaerythritol, polyglycerol, or sorbitol under basic conditions.

The starting polyether may be derivatized to contain a suitable leaving group by reaction with its hydroxyl groups using methods well known in the art. Suitable leaving groups are those capable of being displaced by 1-thioglycerol, and include, but are not limited to, chloride, bromide, iodide, methanesulfonate (mesylate), and toluenesulfonate (tosylate). For example, the starting polyether can be reacted with thionyl chloride in a suitable solvent such as dichloromethane or toluene to form the chloride derivative, as described in detail in Examples 1 and 2 herein. Alternatively, the starting polyether may be reacted with methanesulfonyl chloride in a suitable solvent, such as dichloromethane, in the presence of a base such as tripentylamine, to form the mesylate derivative. The resulting derivatized polyether has one or more leaving groups capable of being displaced by 1-thioglycerol. In some embodiments, the polyether having one or more leaving groups is a linear or branched polyethylene glycol derivative.

At least one polyether having one or more leaving groups is then reacted with 1-thioglycerol (CAS No. 96-27-5) at a temperature of about 50° C. to about 100° C., more particularly from about 90° C. to about 100° C., in the presence of an equivalent (based on 1-thioglycerol) of a base capable of deprotonating the hydrosulfide group in 1-thioglycerol, and an optional solvent for a time sufficient to form a thiomethylethylene glycol-functionalized polyether having at least one glycol group. The time required for the reaction will depend on a number of variables including the temperature used and may be determined by one skilled in the art using routine experimentation. Suitable bases include, but are not limited to, sodium bicarbonate, sodium carbonate, sodium hydroxide, potassium bicarbonate, potassium carbonate, and potassium hydroxide. The reaction may be carried out in an optional solvent. Suitable solvents include, but are not limited to, water, methanol, ethanol, isopropanol, tetrahydrofuran, and mixtures thereof. The thiomethylethylene glycol-functionalized polyether is separated from the optional solvent and unreacted 1-thioglycerol using methods known in the art, for example, solvent extraction, precipitation, recrystallization, and the like.

The thiomethylethylene glycol-functionalized polyether is then oxidized with about one equivalent of an oxidizing agent per glycol group at a temperature of about 0° C. to about 50° C., more particularly about 0° C. to about 25° C., in an aqueous solution for a period of time sufficient to form the aldehyde-functionalized polyether. The time required for the reaction will depend on a number of variables including the temperature used and may be determined by one skilled in the art using routine experimentation. Suitable oxidizing agents are capable of converting the glycol groups of the thiomethylethylene glycol-functionalized polyether to aldehyde groups, and include, but are not limited to sodium periodate, potassium periodate, periodic acid, phenyl iodosoacetate, and sodium bismuthate. In one embodiment, the oxidizing agent is selected from the group consisting of sodium periodate, potassium periodate, and periodic acid. Preferably, an excess of oxidizing agent is avoided to prevent over-oxidation of the sulfide to form the sulfoxide; this group is unstable with respect to self-condensation due to the acidic methylene between the aldehyde and sulfoxide groups. The final aldehyde-functionalized polyether may be recovered from the aqueous reaction mixture using methods known in the art, for example, solvent extraction, precipitation, recrystallization, and the like.

Uses of Aldehyde-Functionalized Polyethers

The aldehyde-functionalized polyethers disclosed herein may be used for a variety of applications such as protein conjugation to attach polyethers, in particular polyethylene glycols, to therapeutic proteins to reduce the rate of clearance of the protein from the body and to reduce the antigenicity of the protein (see for example, Rosen et al. (U.S. Pat. No. 7,217,845). In addition, the aldehyde-functionalized polyethers may be used to modify the properties of surfaces, for example to make them more hydrophilic, by reaction with amine groups on the surface. In these applications where the aldehyde-functionalized polyether is used as a modifier of the hydrophilic-lipophilic balance of a protein or a surface, aldehyde-functionalized polyethers having the higher molecular weight ranges given above for the polymeric segment or the polymeric arms in general formulae (1) and (2) may be more useful.

Additionally, the aldehyde-functionalized polyethers may be used in combination with a second component containing primary amine groups to form a crosslinked hydrogel which may be useful for medical and veterinary applications (see for example, Rhee et al., U.S. Pat. Nos. 5,324,775; 5,874,500; and 6,534,591; and Kodokian et al., U.S. Patent Application Publication No. 2006/0078536). Medical applications include, but are not limited to, wound closure, supplementing or replacing sutures or staples in internal surgical procedures such as intestinal anastomosis and vascular anastomosis, tissue repair, ophthalmic procedures, and as a plug to seal a fistula or the punctum. Additionally, the hydrogels may have utility in drug delivery and in anti-adhesive applications. For example, an aldehyde-functionalized polyether can be reacted with an amine-containing polymer such as a poly(vinyl alcohol-co-vinyl amine) or an aminated polysaccharide such as aminated dextran to form a hydrogel sealant. The two components may be used in the form of two aqueous solutions or dispersions or can be incorporated into an anhydrous fibrous sheet, as described in Examples 4 and 5 herein. In these applications where the aldehyde-functionalized polyether is used as a crosslinking agent to form a hydrogel, aldehyde-functionalized polyethers having the lower molecular weight ranges given above for the polymeric segment or the polymeric arms in general formulae (1) and (2) may be more useful.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

A reference to "Aldrich" or a reference to "Sigma" means the said chemical or ingredient was obtained from Sigma-Aldrich, St. Louis, Mo.

Reagent Preparation

Preparation of Poly(vinyl alcohol-co-vinyl amine):

A copolymer of vinyl alcohol and vinyl amine was made by copolymerizing vinyl acetate and N-vinylformamide followed by hydrolysis. A thiol chain transfer agent was employed to limit polymer molecular weight and provide a practical spinning solution viscosity.

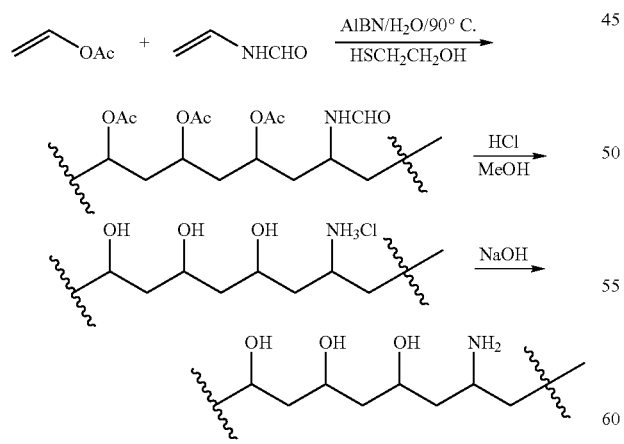

A solution of 0.1 g sodium dodecylbenzenesulfonate in 80 mL of deionized water was placed in a 250-mL, 4-neck round-bottom flask with condenser and nitrogen inlet, thermometer, 2 dropping funnels and a magnetic stirrer. The flask was swept with nitrogen and stirred in a 90° C. oil bath until the solution temperature was 90° C.; then 0.1 g of AIBN (2,2'-azobisisobutyronitrile; Aldrich 441090) initiator was added. A solution of 32 g vinyl acetate (Aldrich V1503; filtered through basic alumina to remove inhibitor), 5 g N-vinylformamide (Aldrich 447331; as received) and 0.10 mL of 2-mercaptoethanol (Aldrich M3701) was placed in a larger dropping funnel under nitrogen, and a solution of 1.0 g AIBN in 9 mL of vinyl acetate was placed in a smaller dropping funnel. Four milliliters of the thiol-containing monomer solution and 1 mL of the AIBN-containing monomer solution were then added to the flask with stirring and the polymerization proceeded at 90° C. under refluxing vinyl acetate (boiling point of 72° C.). The mixture was stirred for 20 min and another 4 mL+1 mL of the two monomer solutions, respectively, were added, after which the mixture became increasingly opaque white. The 4 mL+1 mL of the two monomer solutions were added every 20 min for 1 hour; then the mixture was stirred for 1 hour at 90° C. After this time, the remainder of the monomers were added at a rate of 4 mL+1 mL every 20 min. When the monomers were all added (about 4 hours), the mixture was stirred at 90° C. for 2 hours more and then the heating bath was removed. The suspension was rotary evaporated to remove monomer and water and the remaining damp sludge was taken up in 250 mL of methanol. An aliquot was precipitated with diethyl ether and dried under high vacuum for analysis by proton NMR and size exclusion chromatography. $^1$H NMR (500 MHz; DMSO-d6): by ratio of the 3.80-ppm N-vinylformamide methine peak to the 4.78-ppm vinyl acetate methine peak, the polymer had 11.2 mol % N-vinylformamide incorporation (hydrolyzed amine EW=390). Size exclusion chromatography (N,N-dimethylacetamide) results: $M_n$=44,700; $M_w$=447,000; $M_z$=2,086,000; $M_w/M_n$=10.0; g'=0.81; α=0.59.

Ten milliliters of concentrated hydrochloric acid was added to the methanol solution of polymer and the resulting mixture was stirred at reflux for 24 hours, during which time a rubbery polymer precipitated and coagulated. Proton NMR (DMSO-d6) showed that the acetate groups were gone. Filtration and drying under nitrogen yielded 18.3 g of product. The product was dissolved in 170 mL of deionized water and the resulting solution was filtered through a 5-μm membrane filter. The filtered solution was basified to pH 9.0 (measured with a pH electrode) with NaOH and the solution was desalted by dialysis against deionized water in a MEMBRA-CELL® (Viskase Companies, Inc., Willowbrooke, Ill.) 3.5K MWCO (molecular weight cut-off) dialysis membrane tube. The dialyzed poly(vinyl alcohol-co-vinyl amine) solution was then adjusted to 20 wt % by rotary evaporation to remove excess water. This polymer solution was kept protected from atmospheric carbon dioxide which would react with the amine groups to form unreactive carbamates.

Example 1

Preparation of an Aldehyde-Functionalized PEG—Four-Arm PEG 2K Tetra(thiomethylaldehyde)

A 4-arm PEG 2K tetra(thiomethylaldehyde) was prepared by reacting 4-arm PEG 2K tetrachloride with 1-thioglycerol to give a 4-arm PEG 2K with thiomethylethyleneglycol ends. Oxidation of this intermediate with one equivalent of sodium metaperiodate per glycol group yielded the 4-arm PEG 2K terminated with thiomethylaldehyde groups.

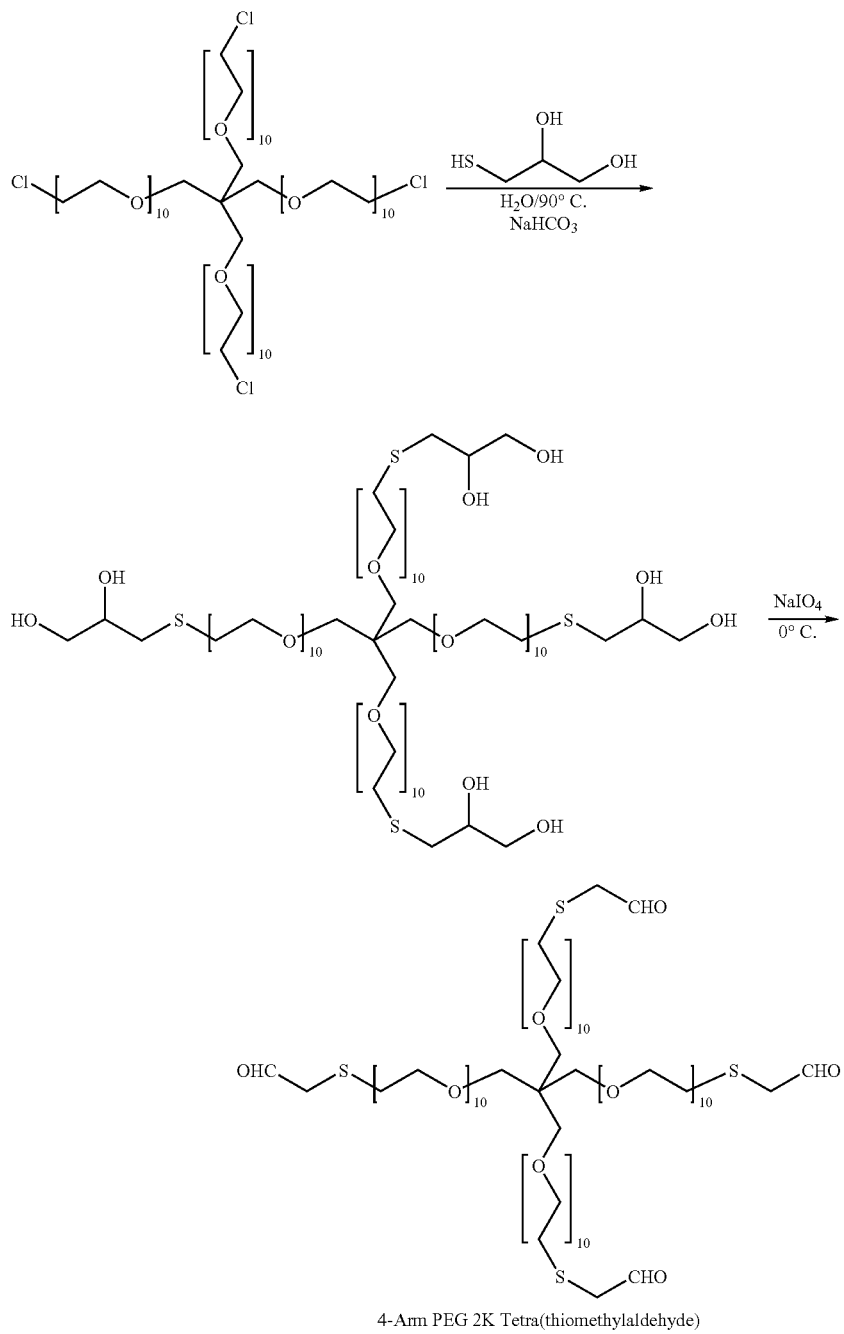

4-Arm PEG 2K Tetra(thiomethylaldehyde)

In the first step, a four-arm PEG 2K tetrachloride was prepared by reacting a four-arm PEG 2K tetraalcohol with thionyl chloride as follows. Four-arm PEG 2K tetraalcohol ($M_n$=2000; SunBright PTE-2000; NOF Corp., Tokyo, Japan), (100 g in a 500-mL round-bottom flask) was dissolved in 100 mL of dichloromethane. Thionyl chloride (88 mL, 1.2 mol) was added, and the mixture was stirred under a blanket of nitrogen at ambient temperature for 24 hours Excess thionyl chloride and dichloromethane were removed by rotary evaporation (bath temp 40° C.). Two successive 50-mL portions of toluene were added and evaporated under reduced pressure (2 kPa, bath temperature 60° C.) to complete the removal of thionyl chloride to give the 4-arm PEG 2K tetrachloride product.

Proton NMR results from one preparation are:

$^1$H NMR (500 MHz, DMSO-d6): δ 3.71-3.68 (m, 8H), 3.67-3.65 (m, 8H), 3.57-3.55 (m, 8H), 3.50 (m, ~140H), 3.47-3.45 (m, 8H), 3.31 (s, 8H).

A solution of 10.0 g (20 mmol Cl) of the 4-arm PEG 2K tetrachloride, 2.5 g (30 mmol) sodium bicarbonate and 3.5 g (32 mmol) 1-thioglycerol (Aldrich M1753) in 30 mL of water was stirred in a 90° C. oil bath under nitrogen for 22 hours. The solution was cooled to room temperature and extracted with three 35-mL portions of dichloromethane. The combined extracts were dried with sodium sulfate followed by magnesium sulfate, filtered, concentrated to 20-25 mL and precipitated with stirring in 500 mL of diethyl ether with chilling in ice. The product was still a liquid at 0° C., so stirring was stopped and the flask was cooled in dry ice. The ether was decanted off the white product which had solidified on the bottom of the flask. The flask was warmed to room temperature and the liquefied product was stirred with 200 mL of fresh ether and chilled again in dry Ice. The ether was decanted off and the product was taken up in dichloromethane (50 mL) and transferred to a round-bottom flask. The solvent was removed by rotary evaporation and the concentrate was held under high vacuum to yield 7.5 g of 4-arm PEG 2K tetra(thiomethylethyleneglycol) as a clear liquid.

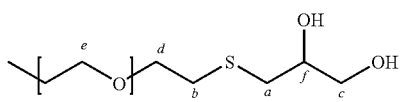

$^1$H NMR (500 mHz; CDCl$_3$): δ 2.70 ppm (ABX q of d, 2H, a); 2.76 (t, J=6.1 Hz, 2H, b); 3.41 (s, pentaerythritol core CH$_2$O, 2H); 3.54 (m, 3H, c); 3.59 (t, J=4.7 Hz, 2H, d); 3.64 (s, 46H, e); 3.75 (t, CH$_2$Cl, gone); 3.81 (m, 1H, f).

A solution of 2.0 g (3.5 mmol diol; EW approximately equal to 575; M$_n$ approximately equal to 2300) 4-arm PEG 2K tetra(thiomethylethyleneglycol) in 20 mL of deionized water was stirred in an ice bath as a solution of 0.75 g (3.5 mmol) sodium metaperiodate in 10 mL of water was added in 3-mL portions every 5 min. The mixture was allowed to stir at 0° C. for 60 min and then 5 drops of ethylene glycol were added and the solution was extracted with four 25-mL portions of dichloromethane. The combined extracts were dried with magnesium sulfate and concentrated by rotary evaporation from a warm tap water bath to about 15 mL. The concentrate was added with stirring to 150 mL of diethyl ether. The mixture was stirred for 15 min and then cooled in dry ice to freeze the product. The ether was decanted off, replaced with 100 mL of fresh ether and the mixture was warmed to room temperature and stirred for 10 min, followed by freezing and decanting again. The product was then taken up in 25 mL of dichloromethane, transferred to a 100-mL round-bottom flask, and rotary evaporated from a warm tap water bath. The concentrate was held under vacuum at 22° C. with a nitrogen bleed through a syringe needle to remove solvent, yielding 1.10 g of liquid 4-arm PEG 2K tetra(thiomethylaldehyde).

Infrared (neat): 1716 cm-1 (CHO)

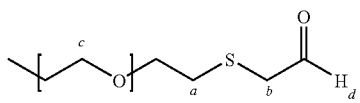

$^1$H NMR (500 MHz; CDCl$_3$): δ 2.66 ppm (t, J=6.1 Hz, 2H, a); 3.27 ppm (d, J=3.5 Hz, 2H, b); 3.64 ppm (s, 46H, c); 9.51 ppm (t, J=3.3 Hz, 0.8H d). As determined from the ratio of the SCH$_2$CHO integral (9.51 ppm) to S(=O)CH$_2$CHO integral (9.86 ppm), the product contained about 12 mol % sulfoxide aldehyde ends because of over-oxidation with excess metaperiodate, due either to incomplete functionalization of the 4-arm PEG 2K chloride with thioglycerol or an inaccurate measurement of the 4-arm PEG 2K tetra(thiomethylethyleneglycol) molecular weight. This compound is somewhat unstable with respect to self-condensation due to the acidic methylene between the aldehyde and sulfoxide, becoming crosslinked upon standing at 22° C. for about a week.

Example 2

Preparation of an Aldehyde-Functionalized PEG—Linear PEG 600 Bis(thiomethylaldehyde)

A low molecular weight linear PEG bis(thiomethylaldehyde) was made by converting the PEG diol to the corresponding dichloride, converting the dichloride to the bis(thiomethylethyleneglycol), which was oxidized to the bis (thiomethylaldehyde).

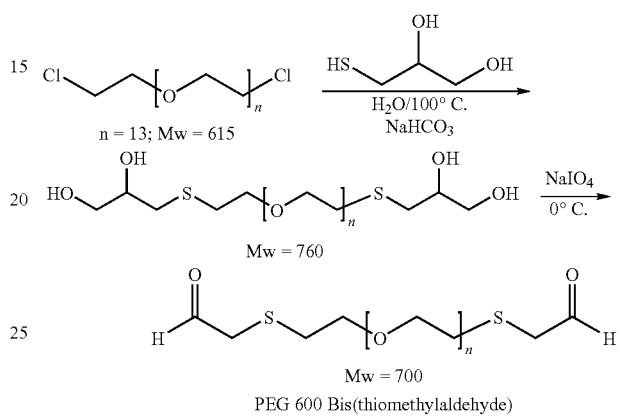

PEG 600 Bis(thiomethylaldehyde)

A solution of 20 g (67 mmol OH) PEG 600 (M$_n$=600; Aldrich 202401) and 0.2 mL of N,N-dimethylacetamide in 60 mL of toluene in a 200-mL round-bottom flask was stirred in a 70° C. oil bath as 7.5 mL of thionyl chloride (12 g; 100 mmol) was added dropwise down the condenser. The solution was stirred under nitrogen at 70° C. for 20 hours. The mixture was rotary evaporated to remove about half of the toluene. The resulting concentrate was added to ether chilled in an ice bath, and then chilled in dry ice to separate a slurry which was quickly filtered cold and then added to 200 mL of hexane. The resulting solid, which was very sticky and low-melting, was taken up in dichloromethane, rotary evaporated and held under vacuum under a nitrogen stream from a needle through a septum to remove solvent. The resulting PEG 600 dichloride (10.4 g) was a brown oil.

$^1$H NMR (500 MHz; CDCl$_3$): δ 3.64 ppm (s, OCH$_2$CH$_2$O backbone; 52H); 3.76 ppm (t, J=5.9 Hz, ClCH$_2$CH$_2$O; 4H).

A solution of 9.0 g (29 mmol Cl) PEG 600 dichloride, 4.0 g (48 mmol) sodium bicarbonate and 4.3 g (40 mmol) 1-thioglycerol (Aldrich M1753) in 25 mL of water was stirred in a 100° C. oil bath under nitrogen for 16 hours. The solution was extracted with four 40-mL portions of dichloromethane. The combined extracts were dried with magnesium sulfate, filtered, concentrated to 20 mL and precipitated from 200 mL of diethyl ether chilled in an ice bath. The product was still a liquid at 0° C., so stirring was stopped and the flask was cooled in dry ice. The ether was decanted off the white product which had solidified on the bottom of the flask. The flask was warmed to room temperature and the liquefied product was stirred with 200 mL of fresh ether and chilled again in dry ice. The ether was decanted off and the product was taken up in dichloromethane (50 mL) and transferred to a round-bottom flask. The solvent was rotary evaporated off and the resulting concentrate was held under vacuum with a nitrogen purge through a syringe needle to yield 7.4 g of PEG 600 bis(thiomethylethyleneglycol).

$^{1}$H NMR (500 MHz; CDCl$_3$): δ 2.71 ppm (ABX q of d, 4H); 2.77 (t, J=6.1 Hz, 4H); 3.55 (m, 2H); 3.64 (s, 52H); 3.69 (t, J=6.2Hz, ~6H); 3.75 (t, CH$_2$Cl, gone); 3.83 (m, 2H).

A solution of 6.00 g (15.8 mmol diol; EW approximately equal to 380; M$_n$ approximately equal to 760) PEG 600 bis (thiomethylethyleneglycol) in 30 mL of deionized water was stirred in an ice bath as a solution of 3.40 g (16 mmol) sodium metaperiodate in 30 mL of water was added at a rate of 1 mL/min using a syringe pump. Following the addition, the mixture was allowed to stir at 0° C. for 60 min and then 10 drops of ethylene glycol were added and the solution was extracted with four 40-mL portions of dichloromethane. The combined extracts were dried with magnesium sulfate and concentrated by rotary evaporation from a warm tap water bath to a volume of about 15 mL. The concentrate was added with stirring to 200 mL of diethyl ether. The mixture was stirred for 15 min and then cooled in dry ice to freeze the product. The ether was decanted off, replaced with 100 mL of fresh ether and the mixture was warmed to room temperature and stirred for 10 min, followed by freezing and decanting again. The product was then taken up in dichloromethane and transferred to a 100-mL round-bottom flask, rotary evaporated from a warm tap water bath, and then held under vacuum at 22° C. with a nitrogen bleed through a syringe needle to remove solvent, which yielded 2.0 g of PEG 600 bis(thiomethylaldehyde) as an orange liquid. Infrared (neat): 1716 cm-1 (CHO).

$^{1}$H NMR (500 MHz; CDCl$_3$): δ 2.66 ppm (t, J=6.2 Hz, 4H); 3.27 (d, J=3.3 Hz, 4H); 3.64 (s, 88H); 9.51 (t, J=3.3 Hz, 2H); There was <1% over-oxidized sulfoxide aldehyde present. This product remained liquid for months at room temperature under nitrogen.

Example 3

Sealing an Incision in a Swine Uterine Horn using a Fibrous Sheet Comprising Poly(vinyl alcohol-co-vinyl amine) and Four-Arm PEG 2K Tetra(thiomethylaldehyde)

The purpose of this Example was to demonstrate the use of a four-arm PEG tetra(thiomethylaldehyde) in combination with a poly(vinyl alcohol-co-vinyl amine) in the form of a non-woven fibrous sheet to seal an incision in a swine uterine horn. When the fibrous sheet was hydrated, the aldehyde groups of the PEG tetra(thiomethylaldehyde) reacted with the amine groups of the poly(vinyl alcohol-co-vinyl amine) to form a crosslinked hydrogel which was effective in sealing the incision in the swine uterine horn. The non-woven fibrous sheet was formed by electro-blown spinning (Kim et al., U.S. Patent Application Publication No. 2005/0067732) a solution containing poly(vinyl alcohol co-vinyl amine) into a fibrous polymer sheet, which was subsequently coated with a solution containing the 4-arm PEG 2K tetra(thiomethylaldehyde).

A solution containing 20 wt % of poly(vinyl alcohol-co-vinyl amine), prepared as described in Reagent Preparation, was electro-blown at 100 kV to give a non-woven fibrous polymer sheet about a millimeter thick having a fiber diameter of about 1-3 μm. The electro-blown spinning apparatus consisted of a 0.016 inch (0.41 mm) metal tube orifice in the center of a polytetrafluoroethylene (PTFE) plate charged at 100 kV relative to a grounded target, which was a rotating 8-inch (20.3 cm) diameter metal drum covered with a REEMAY® spunbonded polyester (Fiberweb Inc., London) support fabric to receive the spun fiber which accumulated to form a non-woven sheet on the drum. The solution containing poly(vinyl alcohol-co-vinyl amine) was fed to the orifice via a plastic syringe pressurized with nitrogen. The orifice was positioned pointing down toward the target drum from 24-36 cm away and a concentric airflow was provided around the outside of the orifice to collimate and direct the fibers toward the metal drum. The current across this gap was typically about 40-60 μA. A nitrogen pressure of about 50 psig (345 kPa) was used to extrude the polymer solution from the spinning orifice at about 1 mL/min in droplets that were attenuated into fibers by the air stream and the electrostatic field. The spinning unit was contained in a clear polycarbonate box. Relative humidity in this spinning chamber was kept at about 10-20% at 25-30° C. by means of two heated nitrogen streams impinging on opposite sides of the metal drum. The resulting non-woven fibrous poly(vinyl alcohol-co-vinyl amine) polymer sheet was stored in a nitrogen-filled glove box and kept protected from atmospheric carbon dioxide. The sheet was very hydrophilic and would cling tenaciously to one's hands if they were even slightly damp.

A 10-cm×12-cm sheet (0.75 g) of the poly(vinyl alcohol-co-vinyl amine) fibrous polymer, which had been stripped from its REEMAY® backing, was placed in a shallow aluminum pan lined with a PTFE sheet. The pan was placed in a nitrogen-filled glove box, and the fibrous sheet was thoroughly wetted with a solution of 0.30 g 4-arm PEG 2K tetra (thiomethylaldehyde), prepared as described in Example 1, in 10 mL of dichloromethane (CHO:NH$_2$=0.31). The wetted sheet was dried under a stream of nitrogen for 15 min and the pan was then placed in a vacuum chamber and evacuated for 20 min, producing a soft, dry-appearing sheet resembling the original fibrous poly(vinyl alcohol-co-vinyl amine) polymer sheet. The fibrous sheet comprising poly(vinyl alcohol co-vinyl amine) and the four-arm PEG 2K tetra(thiomethylaldehyde) was stored in a sealed plastic bag under nitrogen in the glove box until use.

The fibrous sheet comprising poly(vinyl alcohol co-vinyl amine) and 4-arm PEG 2K tetra(thiomethylaldehyde) was cut into 1.5-cm×2-cm rectangular patches. The weights of the patches were about 50-60 mg. The smoother topside of the patch was always applied to the tissue.

The fibrous sheet was used to seal an incision in a swine uterine horn as follows. A 1-cm transverse incision was made with scissors in the center of a 2-inch (5 cm) section of fresh swine uterine horn, obtained from a local grocery, and the uterine horn was connected with a nylon tie to the nipple of a feed line from a syringe pump with a pressure gauge; the other end of the uterine horn was closed with a hemostat clamp. The syringes were filled with dyed water. A single patch was lightly pressed onto the damp swine uterine horn over the 1-cm incision and lightly tamped down around the perimeter to help establish a bond to tissue and then allowed to cure for 1 min before pressure testing. The patched uterine horn was immersed in a large pan of water and water pressure was applied via the syringe pump until the patch leaked as evidenced by a stream of dye from the patched area of the uterine horn. The mean leak pressure for ten trials in this test was 1.79±1.30 psig (12.3±9.0 kPa). This result demonstrates that the four-arm PEG tetra(thiomethylaldehyde) is useful as a hydrogel precursor that when reacted with a poly(vinyl alcohol-co-vinyl amine) forms a hydrogel that is effective in sealing an incision in a swine uterine horn.

Examples 4 and 5

Sealing an Incision in a Swine Uterine Horn using Fibrous Sheets Comprising Poly(vinyl alcohol-co-vinyl amine) and and PEG 600 Bis(thiomethylaldehyde)

The purpose of these Examples was to demonstrate the use of PEG 600 bis(thiomethylaldehyde) in combination with a poly(vinyl alcohol co-vinyl amine) in the form of a nonwoven fibrous sheet to seal an incision in a swine uterine horn. When the fibrous sheet was hydrated, the aldehyde groups of the PEG 600 bis(thiomethylaldehyde) reacted with the amine groups of the poly(vinyl alcohol co-vinyl amine) to form a crosslinked hydrogel which was effective in sealing the incision in the swine uterine horn. Non-woven fibrous sheets were formed by electrospinning a solution containing poly (vinyl alcohol co-vinyl amine) into fibrous polymer sheets, which were subsequently coated with a solution containing the PEG 600 bis(thiomethylaldehyde).

An 8-cm×10-cm sheet (0.48 g) of the poly(vinyl alcohol-co-vinyl amine) fibrous polymer sheet, described in Example 3, which had been stripped from its REEMAY® backing, was placed in a shallow aluminum pan lined with a PTFE sheet. The pan was placed in a nitrogen-filled glove box, and the fibrous sheet was thoroughly wetted with a solution of 0.18 g PEG 600 bis(thiomethylaldehyde), prepared as described in Example 2, in 10 mL of dichloromethane (CHO:$NH_2$=0.49). The wetted sheet was dried under a stream of nitrogen for 15 min and the pan was then placed in a vacuum chamber and evacuated for 10 min, producing a soft, dry-appearing sheet resembling the original sheet of poly(vinyl alcohol-co-vinyl amine) fibrous polymer. This sheet, referred to herein as Sheet A, was stored in a sealed plastic bag under nitrogen in the glove box until use.

A 7-cm×10-cm sheet (0.43 g) of the poly(vinyl alcohol-co-vinyl amine) fibrous polymer sheet, described in Example 3, which had been stripped from its REEMAY® backing, was placed in a shallow aluminum pan lined with a PTFE sheet. The pan was placed in a nitrogen-filled glove box, and the fibrous sheet was thoroughly wetted with a solution of 0.25 g PEG 600 bis(thiomethylaldehyde), prepared as described Example 2, in 10 mL of dichloromethane (CHO:$NH_2$=0.76). The wetted sheet was dried under a stream of nitrogen for 15 min and the pan was then placed in a vacuum chamber and evacuated for 10 min, producing a soft, dry-appearing sheet resembling the original sheet of poly(vinyl alcohol-co-vinyl amine) fibrous polymer. This sheet, referred to herein as Sheet B, was stored in a sealed plastic bag under nitrogen in the glove box until use.

The fibrous sheets A and B were subjected to the swine uterine horn burst test described in Example 3. The fibrous sheets were cut into 1.5-cm×2-cm rectangular pieces. The weights of most of the rectangles were about 60 mg, but there were also some thin patches of about 20-30 mg. The smoother topside of the patch away from the REEMAY® support was always applied to the tissue. A single patch was lightly pressed onto the damp swine uterine horn over the 1-cm incision and lightly tamped down around the perimeter to help establish a bond to the tissue and allowed to cure for 60 sec before pressure testing. In a few experiments, the patch was pressed onto the damp tissue and then the uterine horn section was immediately immersed in water for 60 sec while the patch cured. Burst pressures were as high in those cases as when the patch was cured in air. The mean leak pressures and standard deviations are given in Table 1.

TABLE 1

Leak Pressures of Sealed Incisions in Swine Uterine Horn

| Example | Fibrous Sheet | Number of Trials | Leak Pressure, psig |
|---|---|---|---|
| 4 | A | 10 | 2.17 ± 1.17 (15.0 ± 8.1 kPa) |

TABLE 1-continued

Leak Pressures of Sealed Incisions in Swine Uterine Horn

| Example | Fibrous Sheet | Number of Trials | Leak Pressure, psig |
|---|---|---|---|
| 5 | B | 8 | 1.39 ± 0.91 (9.58 ± 6.27 kPa) |

The results demonstrate that the anhydrous fibrous sheets containing poly(vinyl alcohol-co-vinyl amine) and PEG 600 bis(thiomethylaldehyde) were effective in sealing incisions in swine uterine horn and suggest that the fibrous sheets would be useful as a tissue adhesive and sealant. Adhesion was good in all cases and better than cohesion. A trace of hydrogel adhesive remained on the tissue when a patch was pulled off. The lower PEG 600 bis(thiomethylaldehyde) loading appeared to give higher burst pressures (Example 4) than higher loading (Example 5). Leaks were typically at the edges, due to failure of the patch to conform to the highly-curved tissue surface. It is important for the patch to be in intimate contact with the tissue while it is initially being wetted for good adhesion at the edges. The thinner patches, while lacking the cohesive strength of the thicker patches, conformed and adhered very well to curved tissue surfaces.

What is claimed is:

1. A compound of the formula:

  a)

  b)

wherein:
(i) P is a linear polymeric segment terminating with a methylene group at both ends of said segment, wherein said segment is derived from a polymer selected from the group consisting of: polyethylene oxide, poly(trimethyleneoxide), poly(tetramethyleneoxide), block or random copolymers of polyethylene oxide and polypropylene oxide, and triblock copolymers of polyethylene oxide and polypropylene oxide;
(ii) Q is a core molecule consisting of a polyol containing at least a number m of OH groups and with the hydrogen removed from at least m of said OH groups;
(iii) PA is a linear polymeric arm terminating with a methylene group at both ends of said arm, wherein said arm is derived from a polymer selected from polyethylene oxide, poly(trimethyleneoxide), poly (tetramethyleneoxide), block or random copolymers of polyethylene oxide and polypropylene oxide, and triblock copolymers of polyethylene oxide and polypropylene oxide;
(iv) S is a sulfur atom; and
(v) m =2 to 16.

2. The compound according to claim 1 wherein P is derived from polyethylene oxide.

3. The compound according to claim 1 wherein PA is derived from polyethylene oxide.

4. The compound according to claim 1 wherein P has a number-average molecular weight of about 200 to about 20,000 Daltons.

5. The compound according to claim 1 wherein PA has a number-average molecular weight of about 100 to about 10,000 Daltons.

6. The compound according to claim 1 wherein the compound of formula (a) is a linear polyethylene glycol bis(thiomethylaldehyde) having a number-average molecular weight of about 600 Daltons.

7. The compound according to claim 1 wherein the compound of formula (b) is a four-arm polyethylene glycol tetra (thiomethylaldehyde) having a number-average molecular weight of about 2,000 Daltons.

8. A process for making a compound of claim 1 comprising the steps of:
   a) reacting at a temperature of about 50° C. to about 100° C. in the presence of a base and an optional solvent, 1-thioglycerol and at least one polyether having one or more leaving groups capable of being displaced by the 1-thioglycerol, to form a thiomethylethylene glycol-functionalized polyether having at least one glycol group;
   b) separating the thiomethylethylene glycol-functionalized polyether from the optional solvent and unreacted 1-thioglycerol;
   c) oxidizing the thiomethylethylene glycol-functionalized polyether separated in step (b) with about one equivalent of an oxidizing agent per glycol group, said oxidizing agent being capable of converting said glycol group to an aldehyde group, at a temperature of about 0° C. to about 50° C. in an aqueous solution to form the aldehyde-functionalized polyether; and
   d) recovering said aldehyde-functionalized polyether.

9. The process according to claim 8 wherein the temperature in step (a) is between about 90° C. and about 100° C.

10. The process according to claim 8 wherein the base is selected from the group consisting of sodium bicarbonate, sodium carbonate, sodium hydroxide, potassium bicarbonate, potassium carbonate, and potassium hydroxide.

11. The process according to claim 8 wherein the optional solvent is selected from the group consisting of water, methanol, ethanol, isopropanol, tetrahydrofuran, and mixtures thereof.

12. The process according to claim 8 wherein the one or more leaving groups are selected from the group consisting of chloride, bromide, iodide, mesylate, and tosylate.

13. The process according to claim 8 wherein the oxidizing agent is selected from the group consisting of sodium periodate, potassium periodate, and periodic acid.

14. The process according to claim 8 wherein the temperature in step (c) is about 0° C. to about 25° C.

15. The process according to claim 8 wherein the at least one polyether having one or more leaving groups is a linear or branched polyethylene glycol derivative.

* * * * *